United States Patent [19]

Vincent et al.

[11] Patent Number: 4,902,817

[45] Date of Patent: Feb. 20, 1990

[54] PROCESS FOR THE SYNTHESIS OF ALPHA N ALKYLATED AMINO ACIDS AND ESTERS THEREOF, APPLICATION TO THE SYNTHESIS OF CARBOXYALKYL DIPEPTIDES

[75] Inventors: Michel Vincent, Bagneux; Jean Baliarda, Anthony; Bernard Marchand, Checy; Georges Remond, Versailles, all of France

[73] Assignee: ADIR Et Cie, Neuilly-sur-Seine, France

[21] Appl. No.: 245,353

[22] Filed: Sep. 16, 1988

[30] Foreign Application Priority Data

Sep. 17, 1987 [FR] France ............................ 8712901

[51] Int. Cl.⁴ .......................................... C07C 103/66
[52] U.S. Cl. .................................... 560/171; 562/571
[58] Field of Search ................ 560/171, 155; 562/571

[56] References Cited

FOREIGN PATENT DOCUMENTS 0049658 4/1982 European Pat. Off. .
0117448 9/1984 European Pat. Off. .

*Primary Examiner*—Bruce Gray
*Attorney, Agent, or Firm*—Gordon W. Hueschen

[57] ABSTRACT

Stereoselective process for the industrial synthesis of compounds of formula (I):

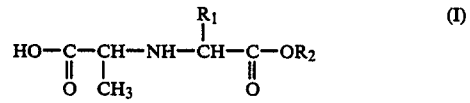

where $R_1$ is linear or branched lower alkyl with 1 to 6 carbon atoms, $R_2$ is a linear or branched lower alkyl with 1 to 4 carbon atoms, employing inexpensive starting materials and obtaining optimum yields.

Application to the synthesis of carboxyalkyl dipeptides.

10 Claims, No Drawings

PROCESS FOR THE SYNTHESIS OF ALPHA N ALKYLATED AMINO ACIDS AND ESTERS THEREOF, APPLICATION TO THE SYNTHESIS OF CARBOXYALKYL DIPEPTIDES

The present invention relates to a process for the industrial synthesis of optionally esterified N-alkylated α-amino diacids and to their application to the industrial synthesis of carboxyalkyl dipeptides.

More specifically, the present invention relates to a new process for the industrial synthesis of compounds of general formula (I):

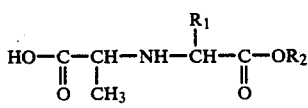

and their addition salts with an acid or base, inorganic or organic,
in which formula:
$R_1$ is linear or branched lower alkyl (with 1 to 6 carbon atoms)
$R_2$ is hydrogen or a linear or branched lower alkyl group (with 1 to 4 carbon atoms).

The derivatives of formula (I) which are obtained according to the process of the invention can be used in the synthesis of carboxyalkyl dipeptides of formula (II):

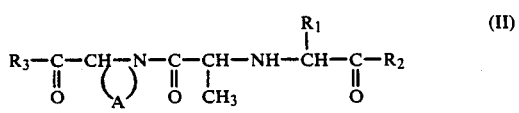

as well as in that of their pharmaceutically acceptable salts,
in which formula:
$R_1$ and $R_2$ have the same meaning as in formula (I),
$R_3$ is a hydrogen atom or a linear or branched lower alkyl group with 1 to 4 carbon atoms,
the structure

denotes indoline, isoindoline, tetrahydroquinoline, tetrahydroisoquinoline, perhydroindole, perhydroisoindole, perhydroisoquinoline, perhydroquinoline, perhydrocyclopenta[b]pyrrole, 2-azabicyclo[2,2,2]octane, or 2-azabicyclo[2,2,1]heptane.

The preferred compound of formula (II) is perindopril of formula (III)

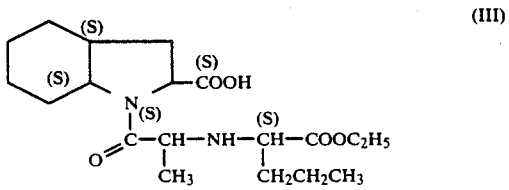

or (2S,3aS,7aS)-1-{2-[1-(ethoxycarbonyl)-(S)-butylamino]-(S)-propionyl}-octahydroindole-2-carboxylic acid, as well as its addition salts with a pharmaceutically acceptable acid or base,
in the case of which the process of the present invention may be applied more particularly.

The compounds of formula (II) as well as their salts have interesting pharmacological properties. In particular, they exert an inhibiting activity on certain enzymes, such as carboxypolypeptidases, enkephalinases or kininase II. In particular, they inhibit the conversion of the angiotensin I decapeptide to angiotensin II octapeptide, which are responsible in certain cases for arterial hypertension, by acting on the conversion enzyme.

The use of these compounds in therapeutics makes it possible, therefore, to reduce or even to suppress the activity of these enzymes, which are responsible for the hypertensive disorder or for cardiac insufficiency. The action on kininase II results in an increase in the circulating bradykinin and also in a lowering in arterial pressure via this route.

Compounds of formula (II) and, more particularly, the compound of formula (III), its preparation and its use in therapeutics have been described in European Patent No. 0,049,658.

The compounds of formula (I) can be used for the preparation of compounds of formula (II).

The compounds of formula (I) comprise two so-called asymmetric carbons, each being capable of having two configurations R or S:

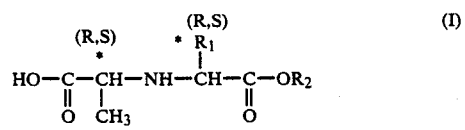

The compounds of formula (I) exist, therefore, in the form of four stereoisomers which may be denoted by (R,R), (R,S), (S,R) or (S,S), according to the configuration of the two so-called asymmetric carbons.

Now, the most active compounds of formula (II) are those in the case of which the two carbons in the side chain both have the S configuration.

This is the reason why the process according to the present invention is concerned more particularly with the industrial synthesis of the compounds of formula (I) in which the two asymmetric carbons both have the S configuration.

Few specific processes for the industrial synthesis of the derivatives of formula (I) have been described. European Patent Application No. 0,117,448, which is very general and which employs α-carboxylated trifluoromethanesulfonates, is known. However, the stereochemistry of both starting materials must be strictly chosen in order to obtain the desired diastereoisomer of the product of formula (I).

It is furthermore known to a person skilled in the art that, as a very general rule, to permit the separation of diastereoisomers which are obtained in the course of syntheses where the stereochemistry of the starting materials is not fixed beforehand, traditional techniques such as fractional crystallization or chromatography on a silica column are resorted to.

The Applicant Company has not found a process for the industrial synthesis of compounds of formula (I) which is of great interest because, on the one hand, it is particularly simple to implement and, on the other hand, because it makes it possible, by a judicious choice of the reactants (catalyst and solvents) which are employed, to obtain the (S, S) diastereoisomer directly in yields which are very advantageous on an industrial scale.

Furthermore, the process according to the invention has the advantage of employing inexpensive compounds as starting materials, and this is of importance on an industrial scale.

More particularly, the process according to the present invention employs as starting material a compound of natural amino acid, of general formula (IV):

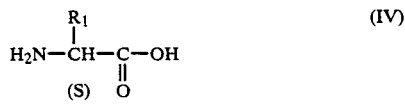

in which $R_1$ has the same meaning as in formula (I), in which the asymmetric carbon has the S configuration since it is well known to a person skilled in the art that the carboxyl-bearing carbon in natural amino acids has the S configuration (with the exception of cysteine), which, when $R_2$ is other than. H, is treated, in the presence of an acidic esterification catalyst, with a lower aliphatic alcohol which is industrially available at a low price, of formula $R'_2OH$, $R'_2$ denoting a lower alkyl group containing from 1 to 4 carbon atoms, to give an ester of formula (V):

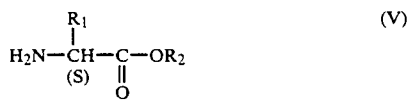

in which
$R_1$ and $R_2$ have the same meaning as in formula (I), which is condensed,
with catalytic hydrogenation under pressure and with slight heating,
in a medium of water or of lower aliphatic alcohol, by itself or mixed with water,
the pressure being between 10 and 100 bars, preferably between 15 and 60 bars,
the temperature being between 10° and 60° C., preferably between 10° and 40° C.,
the catalyst being carefully chosen from nickel, palladium, platinum and rhodium mixed with charcoal so as to direct the selectivity of the reaction, thus making it possible to obtain a maximum proportion of the (S,S) diastereoisomer of the compound of formula (I), with pyruvic acid $CH_3$-CO-COOH, a natural, inexpensive and industrially available product,
to lead directly, after single crystallization in a carefully chosen solvent, cooling and filtration, solely to the (S,S) diastereoisomer of the compound of formula (I).

The example below illustrates the invention, but does not limit it in any way.

EXAMPLE:
N-[(S)-1-CARBETHOXYBUTYL]-(S)-ALANINE

STAGE A: Ethyl L-norvalinate hydrochloride

Place 35 kg of L-norvaline in approximately 300 kg of denatured ethanol in a reactor. Introduce approximately 60 kg of thionyl chloride, slowly and gradually.

After stirring for a quarter of an hour, heat to reflux for 3 hours and then evaporate off the ethanol under vacuum.

Take up the residue with 300 liters of cyclohexane and heat to boiling. After cooling, filter, wash with cyclohexane and dry. 52.9 kg of ethyl L-norvalinate hydrochloride are obtained, that is a 97.6% yield.

The product thus obtained is employed as such in the next stage.

STAGE B: N-[(S)-1-Carbethoxybutyl]-(S)-alanine

Place 45 kg of ethyl L-norvalinate hydrochloride obtained in the preceding stage in approximately 110 liters of water in a vessel equipped with a stirrer.

Alkalify and then pour 23 kg of pyruvic acid very gradually into the solution obtained previously and stir the reaction mixture for 30 minutes.

Place an aqueous suspension of charcoal containing 5% palladium and the alkaline solution of ethyl L-norvalinate obtained previously in a hydrogenation apparatus.

Hydrogenate under pressure (30 bars) at ambient temperature for approximately one day.

Filter under vacuum and evaporate the filtrate down under reduced pressure, filter off and dry. Treat the residue obtained with ethanol; remove the insoluble material consisting of sodium chloride, by filtration and rinse it with ethanol. Combine the ethanolic solutions; evaporate off the ethanol under reduced pressure and crystallize the residue from acetonitrile.

34.3 kg of N-[(S)-1-carbethoxybutyl]-(S)-alanine are obtained, that is a 63.9% yield.

We claim:
1. A process for the synthesis of compounds of formula (I):

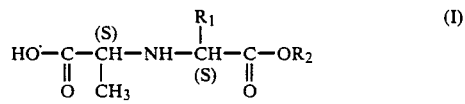

in which:
$R_1$ is linear or branched lower alkyl having 1 to 6 carbon atoms, inclusive,
$R_2$ is hydrogen or a linear or branched lower alkyl group having 1 to 4 carbon atoms, inclusive
the two asymmetric carbon atoms both having the S configuration,
wherein the starting material employed is a compound of formula (IV):

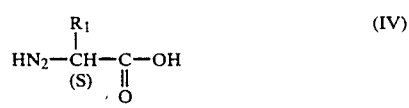

in which:
$R_1$ has the same meaning as in formula (I), the asymmetric carbon having the S configuration, and in which process, when $R_2$ in the product of formula (I) is other than the hydrogen atom, is first esterified, optionally in the presence of an acidic esterification catalyst, with a lower aliphatic alcohol of general formula $R'_2OH$ in which $R'_2$ denotes a linear or branched lower alkyl group having 1 to 4 carbon atoms, inclusive,
to obtain a compound of formula (V):

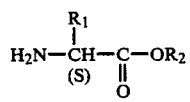

in which:

$R_1$ and $R_2$ have the same meaning as in formula (I), the asymmetric carbon having the S configuration, and in which process the compound of formula V is then condensed with pyruvic acid by catalytic hydrogenation under pressure and with slight heating, the pressure being between 10 and 100 bars, the temperature being between 10° and 60° C., in an aqueous or lower aliphatic alcohol medium, by itself or mixed with water, the catalyst being selected from nickel, platinum, palladium or rhodium, mixed with a support to produce a high proportion of the diastereoisomer of the compound of formula (I) in which the two asymmetric carbons have the S configuration.

2. A process as claimed in claim 1, formula (I) in which:

$R_1$ is an n-propyl group, $R_2$ is an ethyl group.

3. A process as claimed in claim 1, wherein the esterification of the derivative of formula (IV) with ethanol is performed in the presence of thionyl chloride.

4. A process as claimed in claim 1, wherein the catalyst chosen for the catalytic hydrogenation is charcoal containing 5% palladium.

5. A process as claimed in claim 1, wherein the solvent chosen for the catalytic hydrogenation is water.

6. A process as claimed in claim 1, wherein the pressure chosen for the catalytic hydrogenation is between 15 and 60 bars.

7. A process as claimed in claim 1, wherein the temperature chosen for the catalytic hydrogenation is between 10° and 40° C.

8. A process as claimed in claim 1, for the synthesis of the compound of formula (I) in which:

$R_1$ is an n-propyl group, $R_2$ is an ethyl group, wherein, as the last process step, the desired product of formula (I) is purified by a single crystallization from acetonitrile.

9. A process as claimed in claim 1, wherein the catalyst support is charcoal.

10. A process as claimed in claim 1, wherein the desired diastereoisomer is finally obtained by crystallization from at least one hydrous or anhydrous polar organic solvent selected from acetonitrile, ethyl acetate, and a lower-aliphatic alcohol, provided that any mixture employed forms a single phase.

* * * * *

UNITED STATES PATENT AND TRADEMARK OFFICE
CERTIFICATE OF CORRECTION

PATENT NO. : 4,902,817

DATED : February 20, 1990

INVENTOR(S) : Michel Vincent, Jean Baliarda, Bernard Marchand, Georges Remond

It is certified that error appears in the above-identified patent and that said Letters Patent is hereby corrected as shown below:

Column 2, line 5;  "(II)" should read -- (II), --.

Column 2, line 5;  "salts" should read -- salts, --.

Column 3, line 22; "than." should read -- than --.

Column 4, line 45; "inclusive" should read -- inclusive, --.

Column 5, line 26; "1, formula (I) in" should read -- 1, in --.

Signed and Sealed this

Nineteenth Day of March, 1991

Attest:

HARRY F. MANBECK, JR.

Attesting Officer

Commissioner of Patents and Trademarks